(12) United States Patent
Lubitz

(10) Patent No.: US 7,968,323 B2
(45) Date of Patent: Jun. 28, 2011

(54) BACTERIAL GHOST (BG) PRODUCTION PROCESS USING BETAPROPIOLACTONE (BPL) FOR FINAL INACTIVATION

(76) Inventor: Werner Lubitz, Kritzendorf (AT)

( * ) Notice: Subject to any disclaimer, the term of this patent is extended or adjusted under 35 U.S.C. 154(b) by 207 days.

(21) Appl. No.: 12/356,703

(22) Filed: Jan. 21, 2009

(65) Prior Publication Data

US 2010/0092516 A1  Apr. 15, 2010

Related U.S. Application Data

(60) Provisional application No. 61/021,977, filed on Jan. 18, 2008.

(51) Int. Cl.
*C12N 1/00* (2006.01)
*C12N 1/12* (2006.01)
*C12N 15/00* (2006.01)
*C12N 15/01* (2006.01)

(52) U.S. Cl. ............... 435/243; 435/252.1; 435/440; 435/441

(58) Field of Classification Search .................. None
See application file for complete search history.

(56) References Cited

U.S. PATENT DOCUMENTS 2,989,435 A    6/1961  Walop et al.

FOREIGN PATENT DOCUMENTS

| EP | 0 460 480 A2 | 12/1991 |
| WO | 03/006630 A2 | 1/2003 |
| WO | 2005/001059 A2 | 1/2005 |

*Primary Examiner* — Mark Navarro

(74) *Attorney, Agent, or Firm* — Rothwell, Figg, Ernst & Manbeck, P.C.

(57) ABSTRACT

The invention relates to bacterial ghost preparation using betapropiolactone for final inactivation of bacteria.

26 Claims, 11 Drawing Sheets

Figure 1:
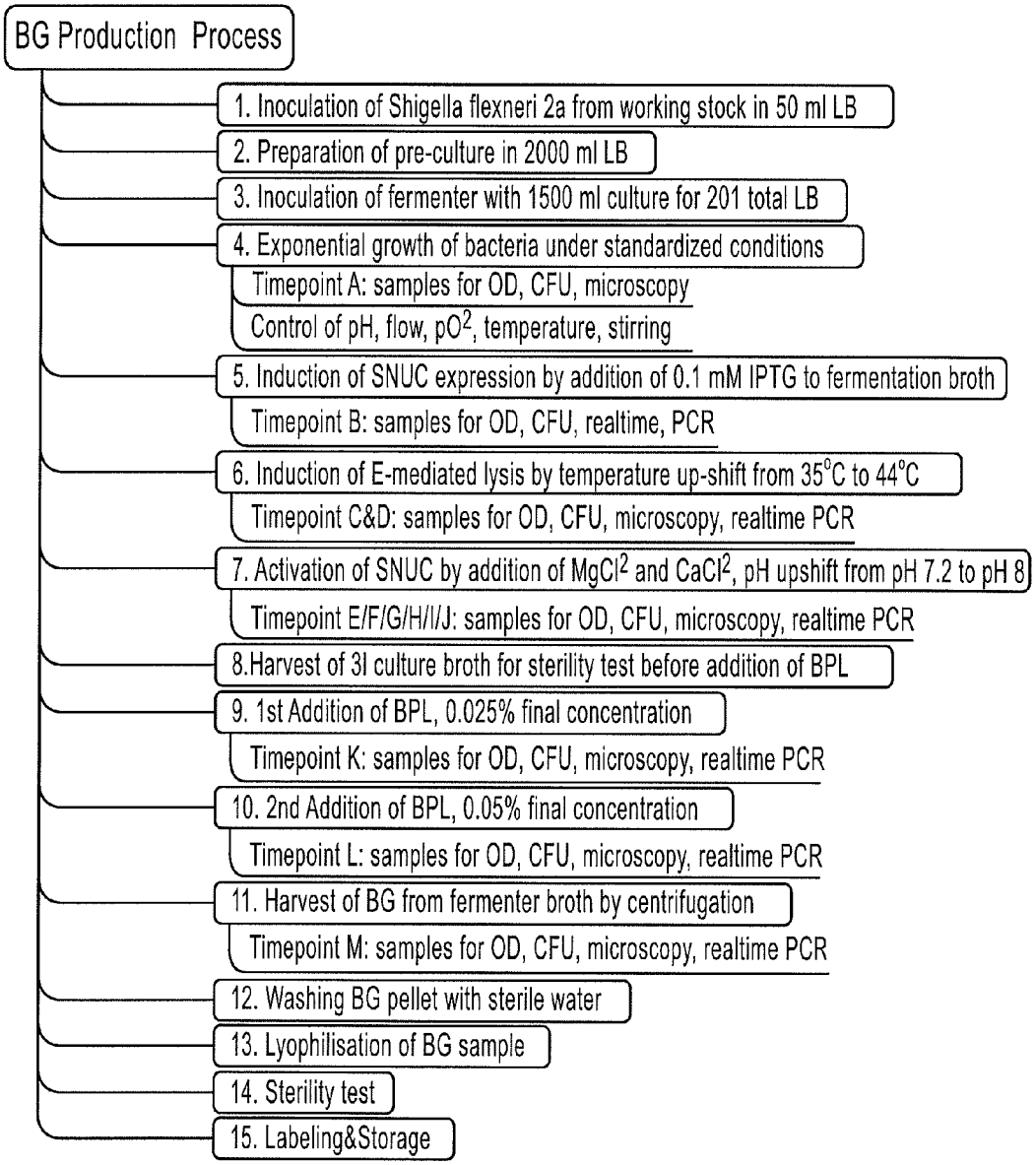
Figure 2:
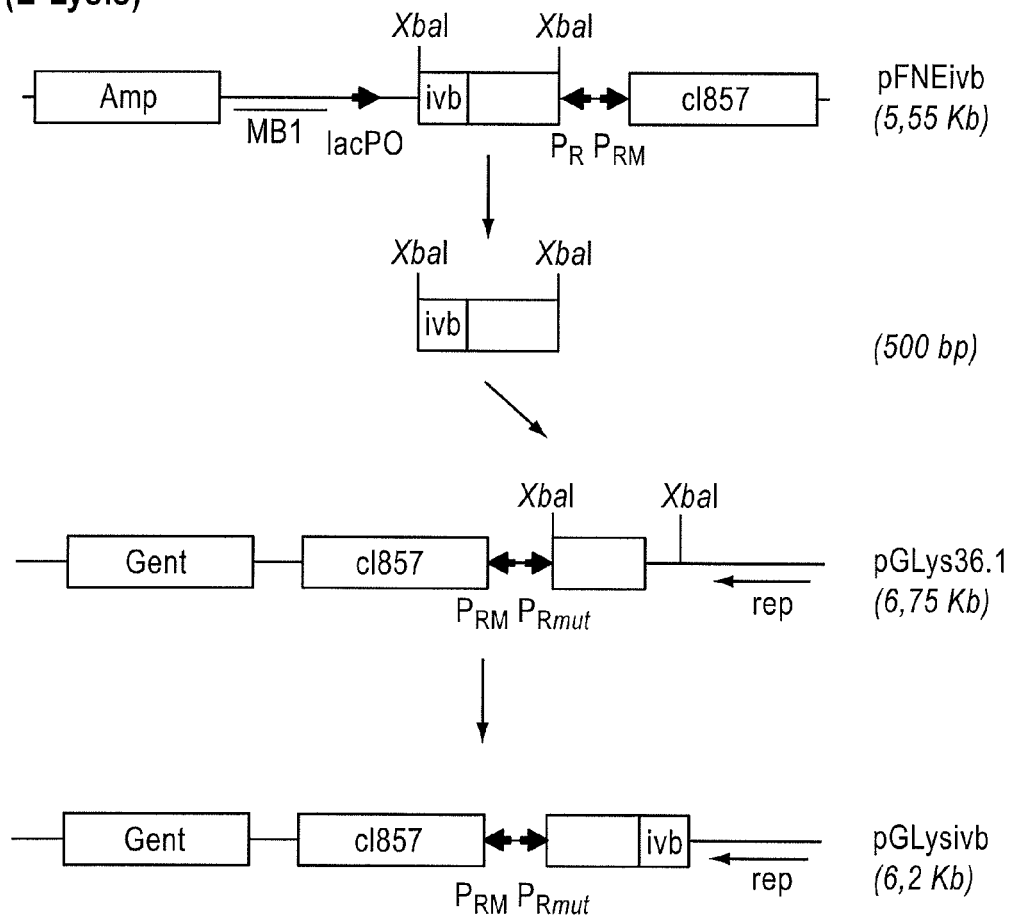

| Zeit: | Min: | | Mean OD NM522 pGLysivb BPL untreated | Mean OD NM522 pGLysivb BPL treated | Mean CFU NM522 pGLysivb BPL untreated | Mean CFU NM522 pGLysivb BPL treated |
|---|---|---|---|---|---|---|
| 11:10 | -100 | OD~0.1 | 0,065 | | | |
| 12:15 | -35 | OD~0,25 | 0,265 | | 7.87E+07 | |
| 12:50 | 0 | OD~0,4 | 0,425 | | 2,87E+08 | |
| 13:20 | 30 | | 0,3 | | 1,72E+06 | |
| 13:50 | 60 | | 0,2 | | 3,30E+05 | |
| 14:20 | 90 | | 0,19 | 0,19 | 1,42E+05 | 1,42E+05 |
| 14:50 | 120 | | 0,18 | 0,19 | 8,63E+04 | 1,00E-01 |
| 15:20 | 150 | | 0,175 | 0,235 | 3,84E+04 | 1,00E-01 |

BACTERIAL GHOST (BG) PRODUCTION PROCESS USING BETAPROPIOLACTONE (BPL) FOR FINAL INACTIVATION

CROSS REFERENCE TO RELATED APPLICATION

This application claims the benefit of U.S. Ser. No. 61/021,977 filed Jan. 18, 2008, the disclosure of which is incorporated herein in its entirety by reference.

The invention relates to bacterial ghost preparation using betapropiolactone for final inactivation of bacteria.

Empty bacterial cell envelopes of gram-negative bacteria, so-called bacterial ghosts (BG), are prepared by controlled heterologous expression of a gene which effects a partial lysis of the bacteria, particularly gram-negative bacteria (EP-A-0 291 021, EP-A-0 516 655). For example, the lytic gene may be the bacteriophage PhiX174 gene E encoding a polypeptide which is inserted into the cell envelope complex of gram-negative bacteria and leads to the formation of a transmembrane tunnel structure through the inner and outer membrane. The inner diameter of this tunnel structure is in the range of about 20-400 nm, particularly 40-200 nm or 500-1,000 nm depending on the lysis conditions applied. The cytoplasmic components are liberated by means of this tunnel structure, wherein an empty cell envelope complex having an intact morphology, a so-called bacterial ghost, is obtained.

Although the lytic process leading to a BG without cytoplasmic content is quite effective, a certain amount, usually about one cell in $10^4$ cells, remains intact. Regulated co-expression of a bacterial lysis gene, e.g. the bacteriophage PhiX174 gene E and a nuclease gene in order to generate nucleic acid free bacterial ghosts results in a synergistic increase of efficiency of the killing process and correspondingly in a substantial reduction of living bacterial cells in a BG preparation as disclosed in WO 03/006630.

The use of bacterial ghosts as dead vaccines or adjuvants and the preparation of recombinant bacterial ghosts carrying heterologous proteins in their cell envelope structures is disclosed in WO 91/13155 and WO 93/01791. Bacterial ghosts are further suitable as carriers or targeting vehicles for active compounds as described in WO 00/53163.

In order to render the use of bacterial ghosts as dead vaccines even safer, particularly for applications in human medicine, it is necessary to provide BG preparations, devoid of living bacterial cells.

Therefore, the technical problem underlying the present invention was to provide BG preparations, free of living bacterial cells.

Surprisingly, it was found that virtually all potentially non-killed bacteria are inactivated when a sterilant was used as a final step in the BG production process, wherein said sterilant is betapropiolactone (BPL). Further surprisingly, integrity of bacterial ghost preparation is maintained following betapropiolactone treatment.

The chemical formula for betapropiolactone is $C_3H_4O_2$, and its molecular weight is 72.06 g/mol. Betapropiolactone is a colorless liquid that is highly soluble in water, its degradation products are harmless compounds arising from self destruction. Betapropiolactone as a sterilant is used for vaccines, tissue grafts, surgical instruments, and enzymes, of blood plasma, water, milk, and nutrient broth, and as a vapor-phase disinfectant in enclosed spaces. Its sterilizing action is used against vegetative bacteria, pathologic fungi, and viruses.

Thus, a first aspect of the present invention relates to a preparation of bacterial ghosts virtually free of living bacterial cells, comprising treating said bacterial ghosts with betapropiolactone. Preferably, the number of any remaining living bacterial cells in the ghost preparation is reduced by a factor of at least $10^3$, more preferably by $10^4$, even more preferably by $10^5$ and most preferably by $10^6$ or even higher.

In the above described method betapropiolactone is preferably added at a final concentration of 0.01%-1% (v/v) and more preferably of 0.025-0.5% (v/v). Betapropiolactone may be added in one or more steps, e.g. in two consecutive steps to the preparation, wherein the two portions are preferably of equal amount, wherein the second portion of betapropiolactone is added after about 15-45 min, e.g. at about 30 min. The addition of betapropiolactone preferably occurs as a liquid. Addition as a vapor or aerosol or in other forms is possible.

A preferred aspect of the present invention is that bacterial ghosts are inactivated for 10-60 min, more preferably for 15-45 min, even more preferably for 25-35 min.

Furthermore, according to the present invention, betapropiolactone addition is carried out preferably at 15-55° C., more preferably at 26-50° C., more preferably at 35-45° C., even more preferably at 36-44° C., and most preferably at 38-43° C.

The bacterial ghost preparation of the present invention may be prepared by a method comprising the following steps:
(a) providing bacterial cells comprising a gene encoding a lytic protein capable of forming a tunnel structure in the bacterial cell envelope
(b) optionally cultivating the bacterial cells under conditions wherein the lytic gene is not expressed
(c) subjecting the bacterial cell to conditions wherein the lytic gene is expressed and the cytoplasmic components of the bacterial cells are liberated and
(d) obtaining the resulting bacterial ghosts.

A preferred example of a gene encoding the lytic protein is the bacteriophage phiX174 gene E.

Particularly preferred, the bacterial cells used for the above described method of bacterial ghost preparation additionally encode an enzyme capable of hydrolyzing cytoplasmic components in the bacterial cell as described in WO 03/006630. The corresponding method of bacterial ghost preparation comprises the following additional steps:
(a) optionally cultivating the bacterial cells under conditions wherein the enzyme gene is not expressed
(b) subjecting the bacterial cell to conditions wherein the enzyme gene is expressed and the cytoplasmic components of the bacterial cells are degraded.

The gene encoding the hydrolytic enzyme is preferably a nuclease gene, in particular a *Staphylococcus aureus* nuclease gene (WO 03/006630).

In a particularly preferred embodiment, the lytic gene and the enzyme gene are in operative linkage with a regulatable expression control sequence. More preferably, the lytic gene and the enzyme gene are each in operative linkage with a separate regulatable expression control sequence and are on one or several vectors. Thus, the expression of both genes may be initiated separately, e.g. at different times of the cultivation procedure.

Preferably, the cells are cultivated under repressing conditions for both the lytic gene and the enzyme gene. Then, the expression of the enzyme is induced, e.g. when the enzyme gene is under control of a chemically regulatable promoter such as the lac promoter or a derivative thereof by adding an inducer, such as IPTG.

More preferably, the enzyme is expressed in a form which is at least partially inactive and which may be activated at a later stage by addition of a prosthetic group to the culture.

Then, subsequently, e.g. after 20 min up to 1.5 h, particularly preferably after about 45 min, the expression of the lytic gene is induced, e.g. when the lytic gene is in operative linkage with a temperature-regulatable promoter, such as the lambda PR or PL promoter in combination with a modified operator sequence and the temperature-sensitive cI857 repressor (WO 98/07874) by a temperature shift to e.g. 42° C. to 44° C. Then, after about 30 min up to 2 h, e.g. at about 90 min, the enzyme is activated by adding a prosthetic group required for its function, e.g. metal ions, such as $Mg^{2+}$ and/or $Ca^{2+}$. The lytic protein E expression can also be induced by chemicals e. g. arabinose when cloned under a chemical inducible promoter/operator system.

In that context, it is particularly favorable that betapropiolactone-mediated inactivation of non-E-lysed bacteria is effective at both the restrictive and the permissive temperature.

In a further preferred embodiment, betapropiolactone is added after induction of lysis and after activation of the hydrolytic enzyme, if applicable, and prior to or after purification of the bacterial ghost preparation, wherein addition of betapropiolactone prior to purification is preferred. Addition of betapropiolactone after purification requires an additional purification step, e.g. prior to use, further modification and/or lyophilization of the bacterial ghosts.

For large-scale production of ghost preparations, it is preferred to concentrate the ghosts after harvesting, e.g. from a fermenter, by centrifugation, tangential filtration, lyophilisation, spray drying or other methods. After concentration betapropiolactone may be added in amounts and under conditions as specified above.

The invention further relates to a composition comprising a betapropiolactone treated bacterial ghost preparation as described above and a pharmaceutically acceptable carrier, diluent and/or adjuvant. The composition is suitable as a vaccine or an adjuvant, e.g. an immunostimulating compound, which is used either alone or together with an immunogen against which an immune-reaction shall be raised. The composition is suitable for use in human medicine and veterinary medicine. Moreover, the bacterial ghosts free of any living bacterial cells may be used as carriers for therapeutic and diagnostic agents, such as polypeptides (e.g. antibodies, cytokines, interferons, chemokines), enzymes and non-immunogenic or immunogenic polypeptides or peptides, nucleic acids and low molecular weight active substances (e.g. peptides, hormones, antibiotics, antitumor agents, steroids, immunomodulators) as disclosed in WO 2005/011713, wherein bacterial ghosts may be sealed, e.g. as described in WO 01/54672 or WO 2005/011713.

Further, the invention relates to the use of betapropiolactone in the manufacture of bacterial ghost preparation, whereby the bacterial ghost preparation is in particular a pharmaceutical preparation.

It should be noted that the disclosure of all patent and non-patent documents recited in the specification above is incorporated herein by reference.

FIGURE LEGENDS

FIG. 1 Flow chart of BG production process for *Shigella flexneri* 2a BG with E-SNUC expression from plasmid pGLNIc FIG. 2 Construction of plasmid pGLysivb FIG. 3 Representative fermentation graph of *S. flexneri* 2a (pGLNIc) to visualize time-points A-M during the course of BG production process FIG. 4 Comparison of *E. coli* NM522 (pBBR1MCS5, no E-lysis) and *E. coli* BG NM522 (pGlysivb, E-lysis plasmid) treated vs. nontreated with BPL at a final concentration of 0.05% BPL at 42° C.

FIG. 4A *E. coli* NM522 (backbone plasmid pBBR1MCS5, no E-lysis) untreated vs. BPL treated FIG. 4B *E. coli* BG NM522 (pGlysivb, E-lysis plasmid) untreated vs. BPL treated FIG. 5 Temperature study to determine the effect of BPL activity at different temperatures FIG. 6 Comparison of *E. coli* NM522 BG and *E. coli* NM522 produced in 20 l fermenter scale and treatment with BPL at a final concentration of 0.05% BPL at 42° C. for 30 min FIG. 6*a* *E. coli* BG NM522 (pGlysivb, E-lysis plasmid), BPL treated FIG. 6B *E. coli* NM522 (backbone plasmid pBBR1MCS5, no E-lysis), BPL treated FIG. 7 *E. coli* NM522 BG produced by combination of E-lysis and nuclease (E-SNUC) in 20 l fermenter scale were inactivated with a final concentration of 0.025% BPL at 42° C. for 30 min.

FIG. 8 Consistency study of *Shigella flexneri* 2a BG (E-SNUC) production using 0.05% BPL for 30 min for final inactivation FIG. 9 Consistency data of realtime PCR from samples during the course of BG production of *Shigella flexneri* 2a out of 5 fermentations of *S. flexneri* 2a (pGLNIc) mean +/− SD out of 5 realtime PCR runs from corresponding 5 fermentations. d.l=detection limit=0.02 ng DNA/ml.

FIG. 10 Fermentation using *Shigella flexneri* 2a (backbone plasmid pBBR1MCS5) inactivated with 0.05% BPL, as control FIG. 10A ATCC 700930 (pBBR1MCS5) run 1

FIG. 10B ATCC 700930 (pBBR1MCS5) run 2

EXAMPLES

1. Preparation of Bacterial Ghosts (BG) Using a Combination of E-lysis and Nuclease Treatment Followed by Betapropiolactone (BPL) Treatment as a Final Inactivation Step (Visualized in FIG. 1)

Gram negative bacteria (e.g *E. coli* or *Shigella flexneri* 2a in this study) are transformed with plasmid pGlysivb (encoding lysis gene E, construction as described in FIG. 2) or pGLNIc (encoding both the lysis gene E and the *Staphylococcus aureus* nuclease gene SNUC; WO 03/006630). Plasmids, pGlysivb and pGLNIc tightly regulate expression of lysis gene E by a temperature upshift from 35° C. to 42-44° C. under the mutated thermosensitive Lambda-promotor ($\lambda$PRmut) and the expression of SNUC depends on induction from an upstream lac-promotor by addition of IPTG. As a consequence of protein E expression an E-specific tunnel structure between the inner and outer membrane of the bacteria is formed resulting in the expulsion of the cytoplasmic contents, including chromosomal and plasmid DNA, into the culture media under conditions described, at least 99.9% of all bacteria are converted into BG during the E-lysis process. To guarantee nucleic acid free BG a second system is activated in case of pGLNIc making use of the DNA and RNA degrading capabilities of SNUC. The nuclease is expressed −30 min before induction of gene E expression during the exponential growth phase of the bacteria and is activated after completion of E-lysis by addition of magnesiumchloride and calciumchloride. For total inactivation of all potentially non-killed bacteria BPL is added in two portions to the fermentation broth as last step in the BG production process. After 30 min incubation with BPL at 42° C.-44° C., BG are harvested by centrifugation or tangential filtration, washed extensively in sterile water and are lyophilized.

Figure 3:
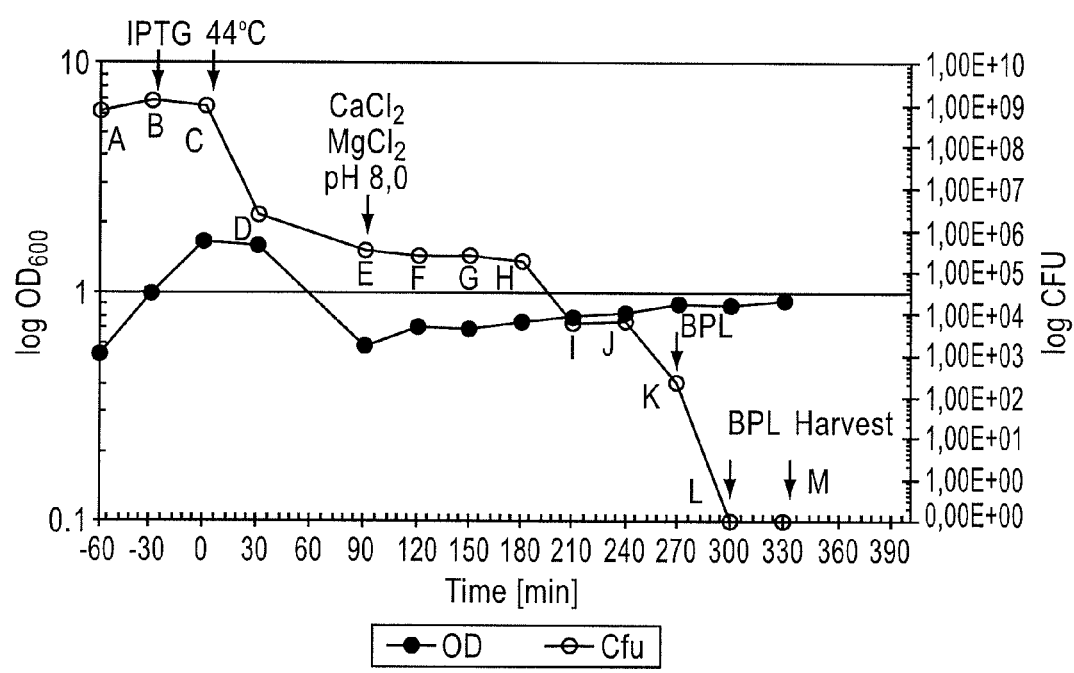

During the production process samples of the culture broth are taken at fixed timepoints (labeled A-M in FIG. 3) to determine optical density, colony forming units (CFU), BG appearance by microscopy as well as for real time PCR analysis of DNA contents. Fermentation parameters like pH, air flow, $pO_2$, stirring and temperature are automatically documented by the fermentation program. Throughout the consistency study all parameters were kept in a narrow window.

In order to see if the final bacterial inactivation by adding BPL before BG harvesting is crucial to the production process 3 l of the culture is withdrawn from the fermenter broth before the addition of BPL, at timepoint K. The culture broth in the vessel is treated with BPL at a final concentration of 0.05% BPL in two additions of 0.025% BPL (timepoint K and L). Adding BPL in two portions is recommended to avoid possible contaminations (e.g by droplet formation under the lid of the vessel) and good inactivation performance. For further analysis of bacterial survival, at timepoint M 3 l of the BG+BPL treated material was harvested (6 bottles each containing 400 ml BG suspension) by centrifugation (15 min at 8,000 rpm).

After centrifugation the supernatant is discarded and the BG pellets are intensively washed in sterile water. In the first washing step each BG pellet is resuspended in 400 ml sterile deionized water and after centrifugation pellets are stored at −20° C. overnight. The following washing steps are to reduce the material to a final volume of 40 ml (washing step 2 in 4×400 ml sterile deionized water, washing step 3 in 2×400 ml sterile deionized water, washing step 4 in 1×400 ml sterile deionized water). Alternatively, the BPL treatment can also occur at this stage of the procedure.

The final pellet is resuspended adding 40 ml sterile deionized water and is distributed to 2 lyophilisation flasks, the remaining sample (.about.5 ml) is transferred to a third lyophilisation flask. After lyophilization the material is examined for sterility. Each sterility testing is done in triplicate. Approximately 10 mg of the BG preparation are filled into labeled, sterile eppendorf tubes. 1.5 ml LBv-medium is added to each tube and the lyophilized material is resuspended. 1 ml of the suspension is poured into an empty Petri dish and 20 ml of LBv agar (cooled down properly to hand warm) is added. After the agar is solid the plate is incubated at 28° C. for 24 h. 100 µl of the BG suspension is used for plating on a LBv agar plate and incubated at 28° C. for 24 h. 200 µl of the ghost suspension is plated on a LBv agar plate and incubated at 28° C. for 24 h. 100 µl of the ghost suspension is used to inoculate 5 ml LBv and incubated for 24 h at 28° C. After the enrichment incubation of the latter medium 100 µl and 200 µl are plated on LBv agar and are incubated at 28° C. for 24 h. The remaining BG suspension is stored at 4° C. Plating and counting of all sterility test plates is performed with WASP system, Don Whitley Scientific, Ltd. equipment.

For realtime PCR, samples of the culture broth were taken during fermentation at timepoints B-M. All realtime PCR runs have been performed according to standardized conditions using Biorad IQ Icycler, amplifiying a fragment of the gentamycin resistance cassette of the lysis/SNUC plasmid pGLNIc. An individual standard curve for pGLNIc quantification was conducted in each realtime PCR run showing a correlation coefficient of at least 0.998.

2. Comparison of *E. coli* NM522 (pBBR1MCS5, no E-lysis) and *E. coli* BG NM522 (pGlysivb, E-lysis Plasmid) Treated vs. Nontreated with BPL at a Final Concentration of 0.05% BPL at 42° C.

Figure 4A:
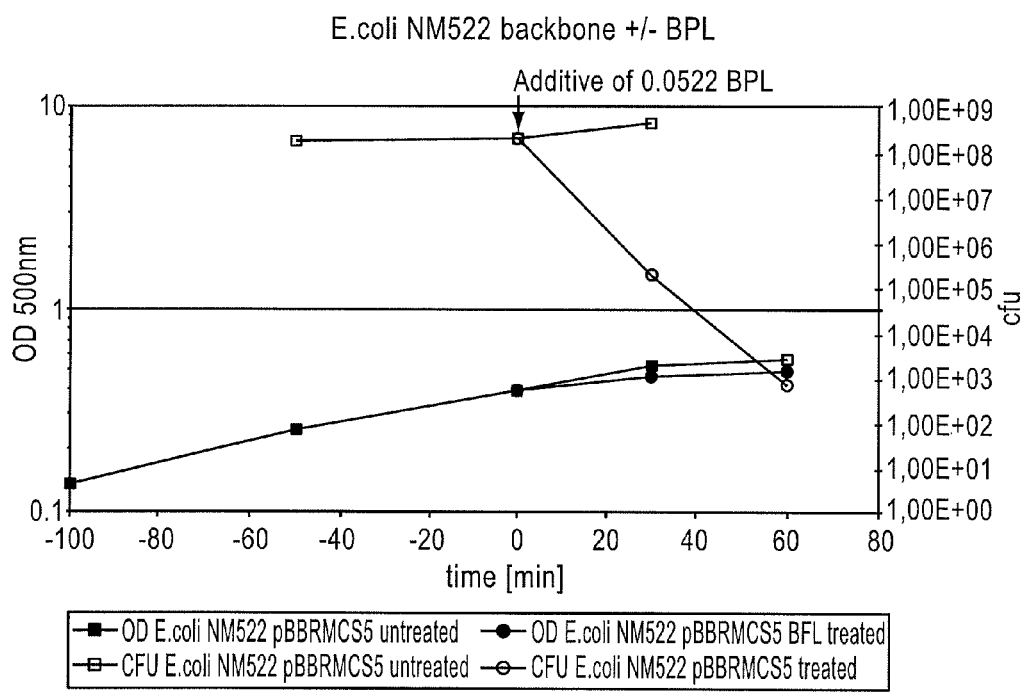
Figure 4B:
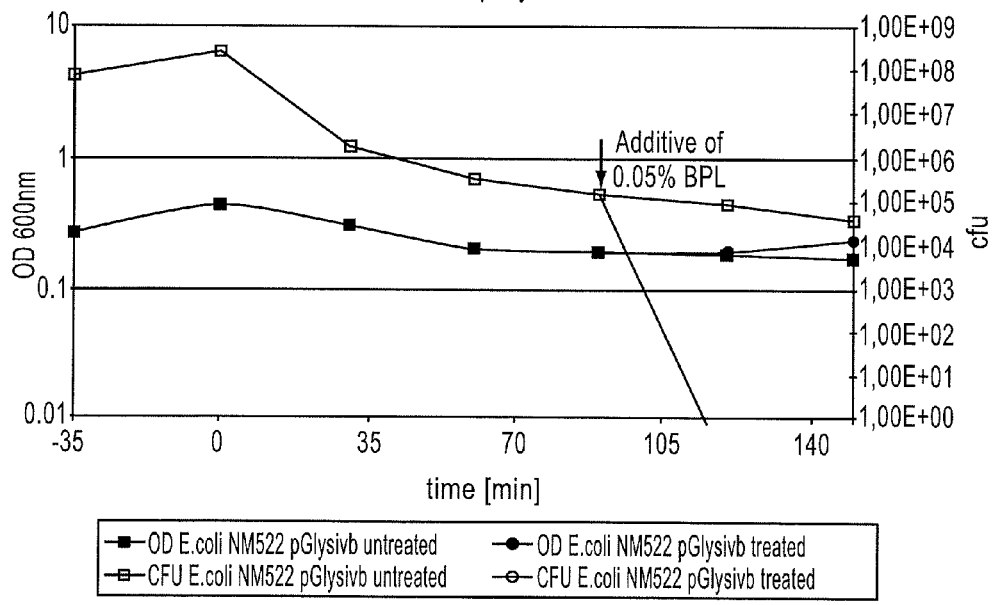

Result:

Data from *E. coli* NM522 (pBBR1MCS5) that have been treated with 0.05% BPL at 42° C. (FIG. 4A) are showing that a reduction in viability of ~5 log is obtained in small scale experiments whereas *E. coli* BG NM522 (pGlysivb) treated with 0.05% BPL at 42° C. (FIG. 4B) are resulting in no surviving bacteria. Using a concentration of 0.05% BPL under a temperature of 42° C. and 30 min for the reaction is sufficient for E-lysed bacteria to be safely inactivated; no living cell counts are detected. Treatment of *E. coli* bacteria with the same amount of BPL under the same parameters does not lead to full inactivation.

3. Temperature Study to Determine the Effect of BPL Activity at Different Temperatures The sterilizing activity of BPL and its self destruction in water is temperature dependant. To prove the temperature profile for bacterial inactivation under conditions for BG production, a study has been conducted to compare inactivation rates of *E. coli* NM522 pGlysivb at a starting CFU of approximately $1 10^3$/ml using 0.05% BPL at 4 different temperatures (16° C., 28° C., 36° C. and 42° C.).

Figure 5:
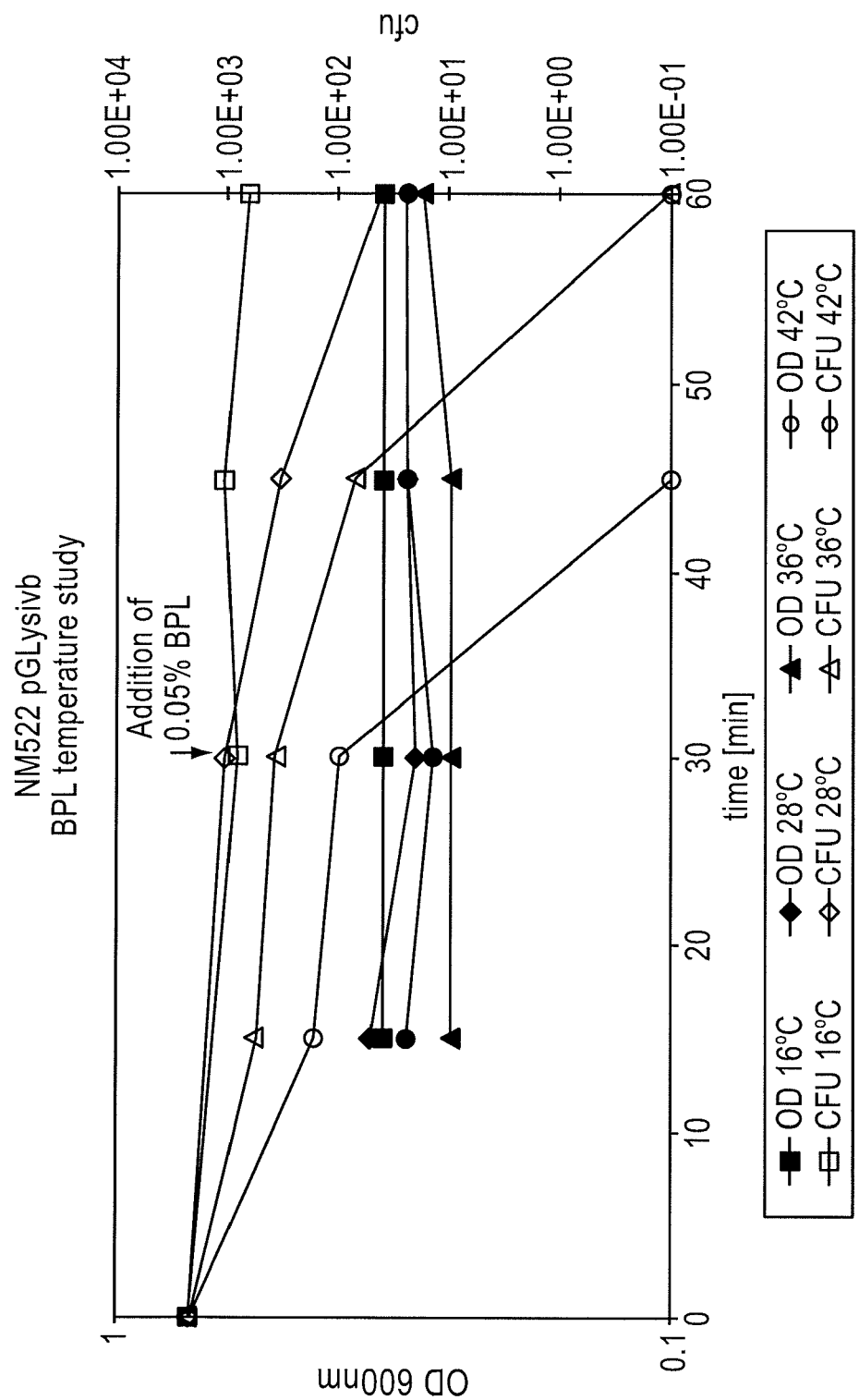

Result:

Fast BPL inactivation rates (15 min) for BG production at 42° C. can be demonstrated in comparison to lower temperatures (30 min at 36° C.) at reduction of CFU by approximately 1.5 log at 28° C. and only slight reduction (less than 0.5 log) at 16° C. within 30 min. A temperature dependant reaction rate has been determined (FIG. 5).

Figure 6A:
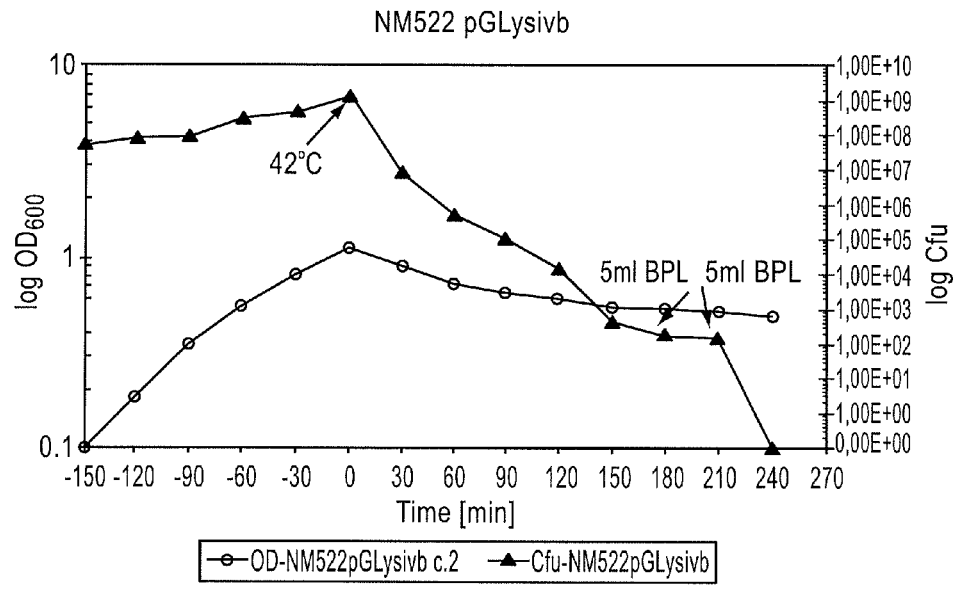
Figure 6B:
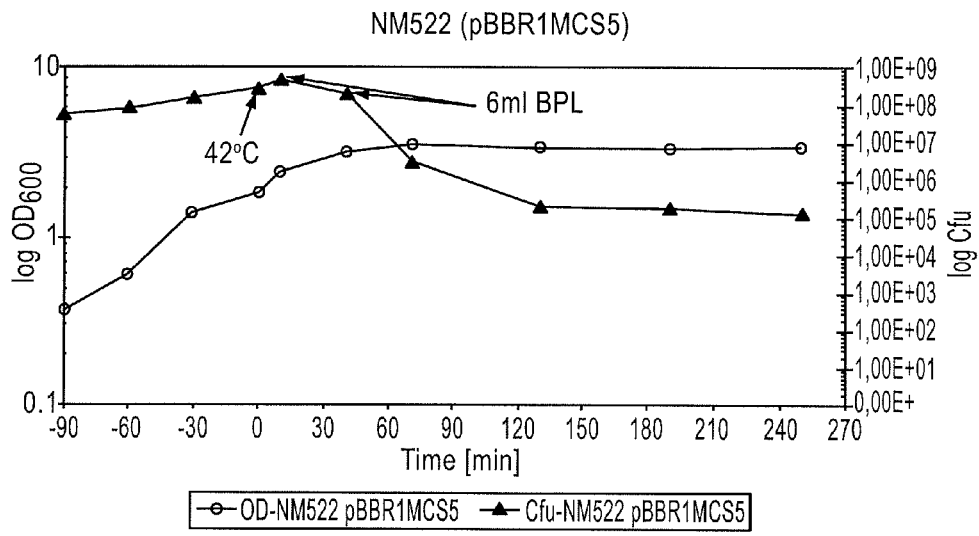

4. Comparison of *E. coli* NM522 BG and *E. coli* NM522 Produced in 20 l Fermenter Scale and Treatment with BPL at a Final Concentration of 0.05% BPL at 42° C. for 30 min To determine the inactivation effect of BPL to *E. coli* NM522 (pBBR1MCS5) under the same fermentation conditions as used for total inactivation of BG produced from *E. coli* NM522 (pGlysivb) (FIG. 6A) control fermentations using *E. coli* NM522 transformed with the backbone plasmid pBBR1MCS5 (no lysis, no nuclease) have been performed (FIG. 6B). BPL killing rates as well as DNA concentration of bacterial samples were measured at time points and under fermentation conditions as described for BG production (Example 1, FIG. 3).

Result:

Data from fermentation of *E. coli* NM522 (backbone plasmid pBBR1MCS5) that have been treated with 0.05% BPL at 42° C. (FIG. 6B) are showing that a reduction in viability of ~3 log is obtained whereas *E. coli* BG produced from NM522 (pGlysivb) treated with 0.05% BPL at 42° C. (FIG. 6A) resulted in total inactivation, no live CFU were detectable at the end of BG production process. (FIG. 6A) For *E. coli* NM522 BG (pGlysivb) in 20 l scale fermenter a final and safe inactivation step for the BG production process can be achieved by using 0.05% BPL for 30 min at 42° C. (FIG. 6B) For *E. coli* NM522 (backbone plasmid pBBR1MCS5) in 20 l scale fermenter no final inactivation of *E. coli* can be achieved by using 0.05% BPL for 30 min at 42° C. The reduction of viability of bacteria is ~3 logs.

5. *E. coli* NM522 BG Produced by Combination of E-lysis and Nuclease (E-SNUC) in 20 l Fermenter Scale Were Inactivated With a Final Concentration of 0.025% BPL at 42° C. for 30 min.

Figure 7:
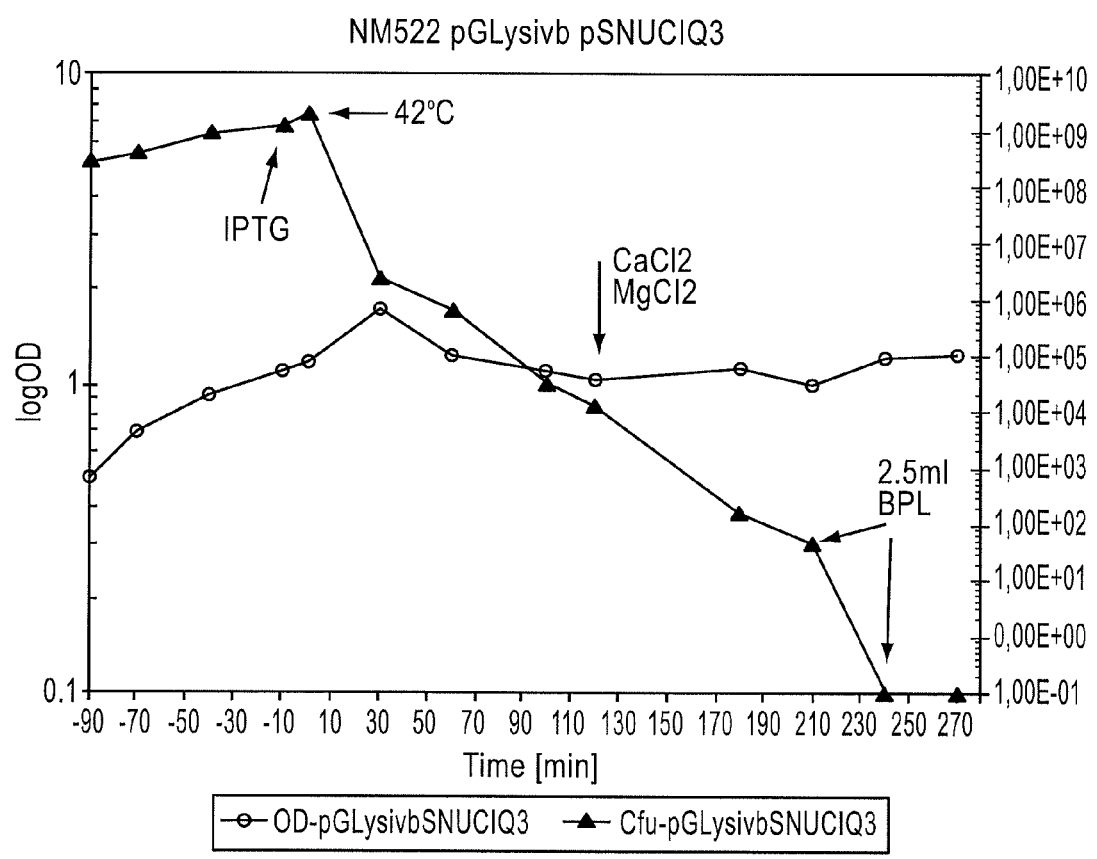
Figure 8:
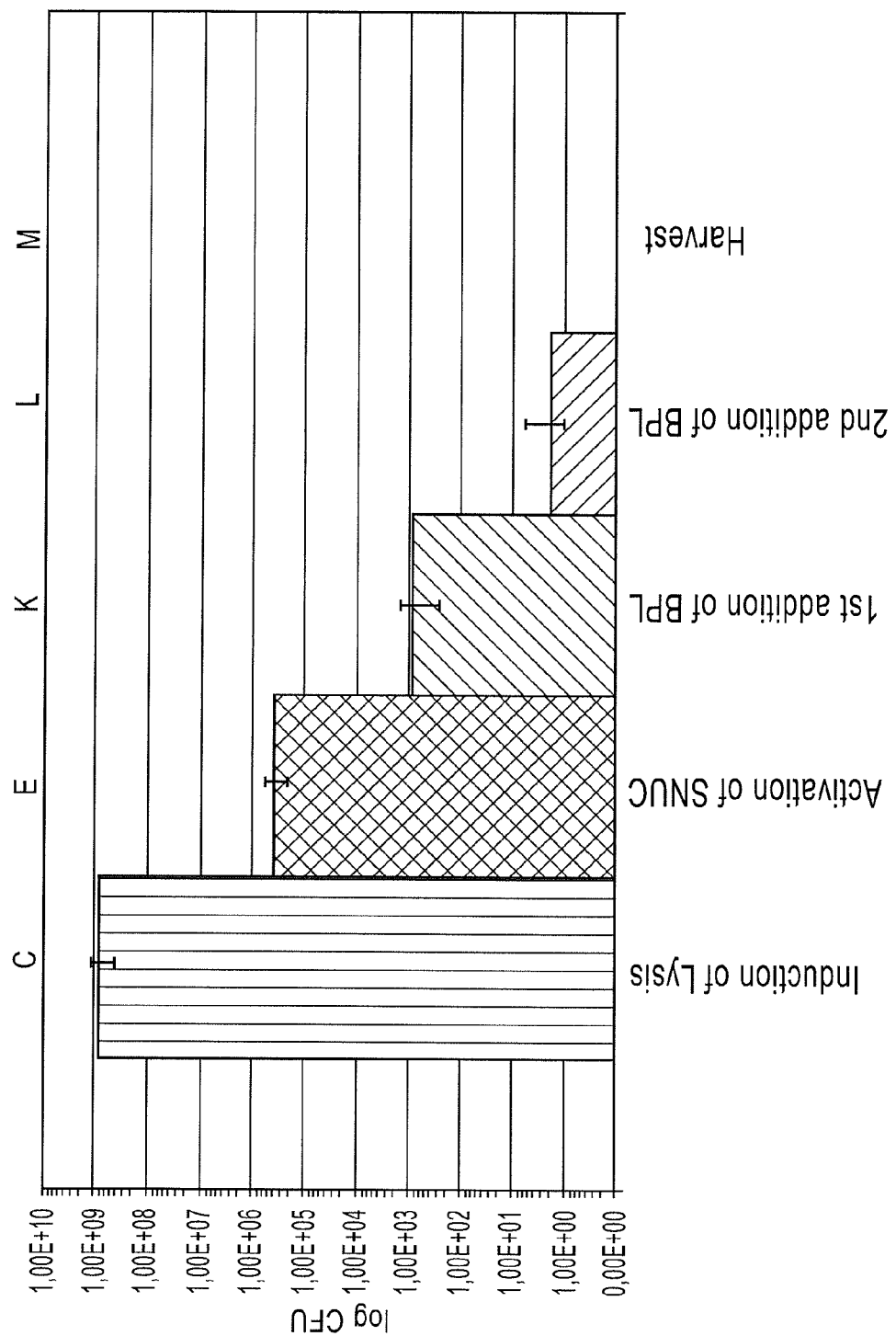
Figure 9:
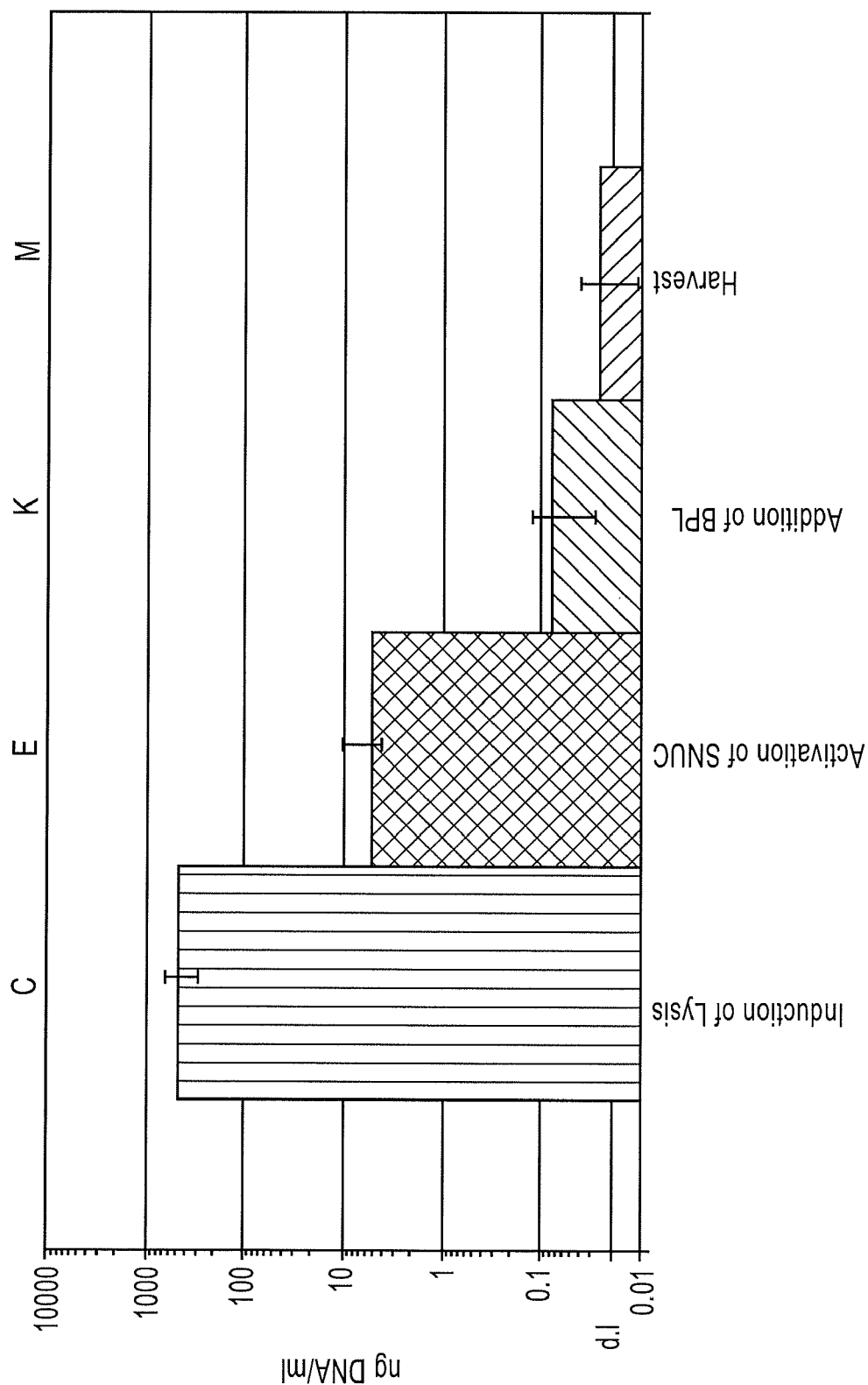
Figure 10A:
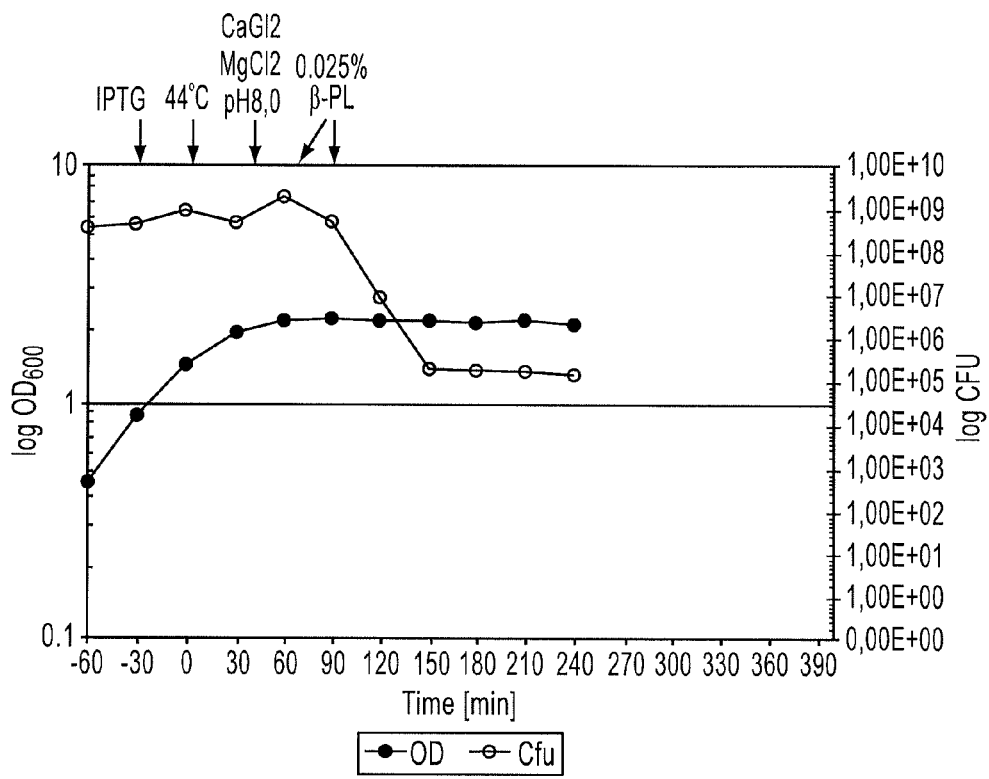
Figure 10B:
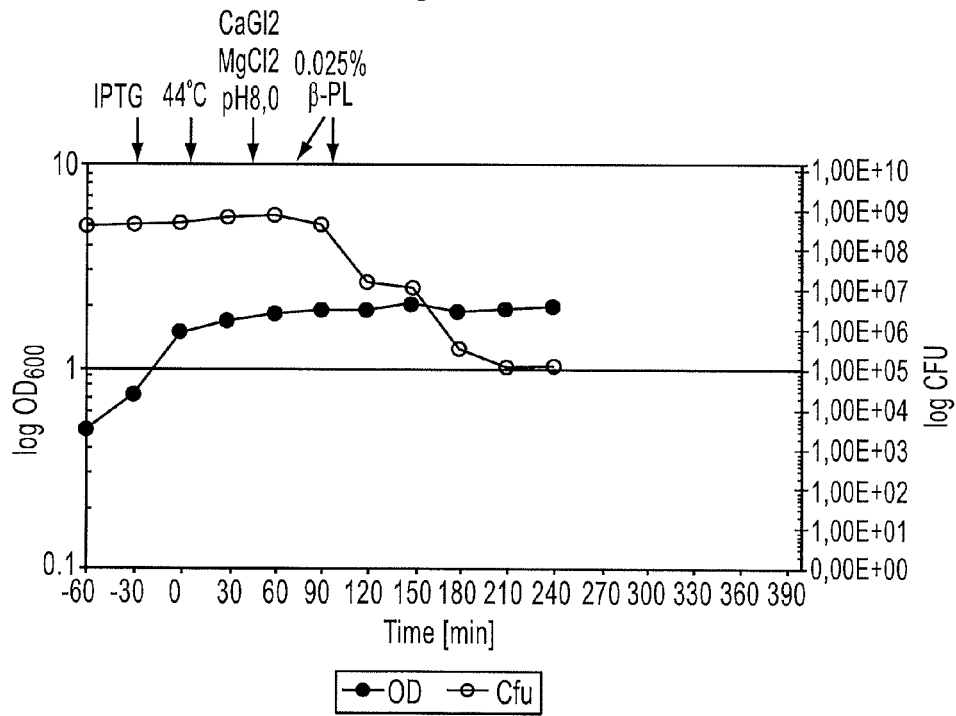

Result:

In the DNA free BG (E-SNUC BG) *E. coli* NM522 (pGlysivb encoding lysis gene E, pSNUCIQ3 encoding *Staphylococcus aureus* nuclease gene SNUC; Mayr et al., 2005) production process of the concentration used for total inactivation by BPL has been determined to be less than 0.025% (FIG. 7). For the production process of DNA free *E. coli* NM522 BG (pGlysivb, pSNUCIQ3) in 20 l scale fermenter a final and safe inactivation can be achieved by using 0.025% BPL for 30 min at 42° C. (FIG. 7).

6. Consistency Study of *Shigella flexneri* 2a BG (E-SNUC) Production Using 0.05% BPL for 30 min for Final Inactivation The consistency study summarizes data from five fermentation runs that were all conducted under the described parameters in the brief description of the BG production process as depicted in FIG. 3 (see Example 1). To visualize the consistency of the fermentations FIG. 8 shows mean CFU values +/−SD at specified sampling points (C=Lysis induction, E=Activation of SNUC, K=1st addition of BPL, L=2nd addition of BPL and M=Harvest). As described above in the manufacturing process (Example 1, FIG. 3), samples during fermentation have been taken at time points B-M for realtime PCR detection to determine residual DNA in the BG samples. To visualize the consistency of the realtime PCR data FIG. 9 shows mean ng DNA/ml of culture harvested +/−SD at specified sampling points (C=Lysis induction, E=Activation of SNUC, K=1st addition of BPL, and M=Harvest).

Result:

The consistency study of *Shigella flexneri* 2a BG production process showed good correlation in consistency for all measured timepoints throughout the production process (FIG. 9). Sterility testings have been performed as described in the brief description of BG production (Example 1, FIG. 3). Material for sterility testing was harvested at two timepoints, at timepoint K, before addition of BPL and at timepoint M at the end of the BG production process. All BG samples tested were found to be sterile. Realtime PCR has been performed to show the reduction of DNA content during the production process. The samples are showing good consistency and the detection limit for DNA (=0.02 ng DNA/ml culture) is reached in the final material of samples taken at timepoint M.

7. Fermentation Using *Shigella flexneri* 2a (pBBR1MCS5) Inactivated with 0.05% BPL, as Control To determine the inactivation effect of BPL to *Shigella flexneri* 2a bacteria under the same fermentation conditions as for production of BG two control fermentations using *Shigella flexneri* 2a transformed with the backbone plasmid pBBR1MCS5 (no lysis, no nuclease) were performed. BPL killing rates as well as DNA concentration of bacterial samples was measured at time points and under fermentation conditions described for BG production (Example 1, FIG. 3).

Result:

For both fermentation of *S. flexneri* 2a (backbone plasmid pBBR1MCS5) the inactivation with 0.05% BPL caused a drop in living cell counts (CFU) by 4 log (FIGS. 10A,B) indicating that in contrast to E-lysis or the combination of E-SNUC lysis, a final concentration of 0.05% BPL alone is not sufficient to kill all bacteria within 30 min.

Realtime data of control fermentations are showing no decline of DNA.

The invention claimed is:

1. A method for producing a bacterial ghost preparation comprising treating said bacterial ghosts with betapropiolactone.

2. The method of claim 1 comprising the steps:

(a) producing a bacterial ghost preparation and (b) subsequently treating the bacterial ghost preparation with betapropiolactone under conditions wherein the number of any remaining living bacterial cells in said ghost preparation is reduced.

3. The method of claim 1, wherein the number of any remaining living bacterial cells in said ghost preparation is reduced by at least $10^3$-$10^4$.

4. The method of claim 1, wherein the bacterial ghosts are treated with 0.01-1% (vlv) betapropiolactone final concentration.

5. The method of claim 1, wherein betapropiolactone addition is carried out in two consecutive steps.

6. The method of claim 1, wherein the betapropiolactone addition is carried out at 26-50° C.

7. The method of claim 1, wherein the bacterial ghosts are inactivated for 10-60 min.

8. The method of claim 1 wherein the bacterial ghost preparation is obtained by:

(a) providing bacterial cells comprising a gene encoding a lytic protein capable of forming a tunnel structure in the bacterial cell envelope complex (b) optionally cultivating the bacterial cells under conditions wherein the lytic gene is not expressed (c) subjecting the bacterial cell to conditions wherein the lytic gene is expressed and the cytoplasmic components of the bacterial cells are liberated and (d) obtaining the resulting bacterial ghosts.

9. The method of claim 8, wherein the gene encoding the lytic protein is the bacteriophage phiX174 gene E.

10. The method of claim 8, wherein the bacterial cells additionally encode an enzyme capable of hydrolyzing cytoplasmic components in the bacterial cell comprising the following steps:

(a) optionally cultivating the bacterial cells under conditions wherein the enzyme gene is not expressed (b) subjecting the bacterial cell to conditions wherein the enzyme gene is expressed and the cytoplasmic components of the bacterial cells are degraded.

11. The method of claim 10, wherein the gene encoding the hydrolytic enzyme is a nuclease gene.

12. The method of claim 8, wherein the lytic gene and the enzyme gene are in operative linkage with a regulatable expression control sequence.

13. The method of claim 12, wherein the lytic gene and the enzyme gene are each in operative linkage with a separate regulatable expression control sequence and are on one or several vectors.

14. The method of claim 13, wherein the expression of the lytic gene and the expression of the enzyme are induced at different times.

15. A pharmaceutical composition comprising a betapropiolactone treated bacterial ghost preparation and a pharmaceutically acceptable carrier, diluent and/or adjuvant.

16. The composition of claim 15, wherein said pharmaceutically acceptable carrier, diluent and/or adjuvant is suitable for use in a vaccine.

17. The composition of claim 15, wherein said pharmaceutically acceptable carrier and/or diluent is suitable for use in an adjuvant.

18. The composition of claim 15, wherein said pharmaceutically acceptable carrier, diluent and/or adjuvant is suitable for use in human medicine.

19. The composition of claim 15, wherein said pharmaceutically acceptable carrier, diluent and/or adjuvant is suitable for use in veterinary medicine.

20. The method of claim 3, wherein the number of any remaining living bacterial cells in said ghost preparation is reduced by at least $10^5$ or $10^6$.

21. The method of claim 4, wherein the bacterial ghosts are treated with 0.025-0.5% (v/v) betapropiolactone final concentration.

22. The method of claim 6, wherein the betapropiolactone addition is carried out at 35-45° C.

23. The method of claim 22, wherein the betapropiolactone addition is carried out at 38-43° C.

24. The method of claim 7, wherein bacterial ghosts are inactivated for 15-45 min.

25. The method of claim 24, wherein bacterial ghosts are inactivated for 25-35 min.

26. The method of claim 11, wherein the gene encoding the hydrolytic enzyme is a *Staphylococcus aureus* nuclease gene.

* * * * *